United States Patent [19]
Vahey et al.

[11] Patent Number: 5,394,247
[45] Date of Patent: Feb. 28, 1995

[54] MEASUREMENT OF PAPER CURL TENDENCY USING SPECULAR AND DIFFUSE LIGHT REFLECTION

[75] Inventors: David W. Vahey, Central Valley, N.Y.; James F. Suska, West Milford, N.J.

[73] Assignee: International Paper Company, Purchase, N.Y.

[21] Appl. No.: 28,471

[22] Filed: Mar. 9, 1993

[51] Int. Cl.$^6$ ................. G01N 21/84; G01B 11/30
[52] U.S. Cl. .................... 356/429; 356/371; 73/159; 162/198; 162/263
[58] Field of Search ............ 356/371, 429; 73/159; 162/198, 263

[56] References Cited

U.S. PATENT DOCUMENTS

| | | | |
|---|---|---|---|
| 3,807,868 | 4/1974 | Simila | 356/118 |
| 4,332,477 | 6/1982 | Sato | 356/371 |
| 4,650,334 | 3/1987 | Alster et al. | 356/376 |
| 4,747,911 | 5/1988 | Polson | 162/263 |
| 4,760,271 | 7/1988 | Brenholdt | 250/571 |
| 4,836,680 | 6/1989 | Tröster et al. | 356/371 |
| 4,978,861 | 12/1990 | Sabater et al. | 356/371 |

FOREIGN PATENT DOCUMENTS

960374 6/1964 United Kingdom.

OTHER PUBLICATIONS

MD/CD Reflectance Anisotropy in Machine-Made Papers Observed with the 45/0 Reflectance Geometry by A. A. Koukoulas and B. D. Jordan, *Journal of Pulp and Paper Science*, vol. 20, No. 3, Mar., 1994.
K. J. Niskanen and J. W. Sadowski Evaluation of Some Fibre Orientation Measurements Journal of Pulp and Paper Science, vol. 15, No. 6, Nov., 1989.
Shigeyoshi Osaki Microwaves Quickly Determine the Fiber Orientation of Paper TAPPI Journal, Feb. 1987.
D. J. Williams The Measurement of Fibre Orientation and its Relation to Directional Strength Properties Appita, vol. 24, No. 3.
Yong Woon Lim, A. Sarko, and R. H. Marchessault Light Scattering by Cellulose TAPPI, vol. 53, No. 12, Dec., 1970.
C. C. Habeger and G. A. Baum The Use of Microwave Attenuation as a Measure of Fiber Orientation Anisotropy TAPPI Journal, Feb., 1987.
R. Boulay, B. Drouin, R. Gagnon and P. Bernard Paper Fibre Orientation Measurement With a Submillimetre Laser Journal of Pulp and Paper Science, vol. 12, No. 1, Jan., 1986.
Claire Schaffnit, Jacques Silvy and C. T. J. Dodson Orientation Density Distributions of Fibres in Paper Nordic Pulp and Paper Research Journal, No. 3, 1992.
J. Waterhouse, S. Stera and D. Brennan Z-Direction Variation of Internal Stress and Properties in Paper Journal of Pulp and Paper Science, vol. 13, Jan., 1987.
P. R. Sundararajan X-Ray Studies on the Orientation of Inorganic Materials in Paper TAPPI, Oct., 1981, vol. 64, No. 10.
E. A. Aaltio, W. Prins and J. J. Hermans X-Ray Investigation into the Orientation of Cellulose Fibers in Paper With Respect to the Plane of the Sheet TAPPI, vol. 42, No. 2, Feb., 1959.
Göran Bryntse and Bo Norman A Method to Measure Variations in Surface and Diffuse Reflectance of Printed and Unprinted Paper Samples TAPPI, Apr., 1976, vol. 59, No. 4.

*Primary Examiner*—Rolf Hille
*Assistant Examiner*—David Ostrowski
*Attorney, Agent, or Firm*—Luedeka, Neely & Graham

[57] ABSTRACT

A method for determining the tendency of a non-woven web to curl, where the web has a machine direction (MD), a cross-machine direction (CD) and the web includes a wire side and a felt side. The method comprises determining a wire ratio which is the ratio of the number of fibers oriented in the MD to the number of fibers oriented in the CD, where the fibers are associated with the wire side of the web, a felt ratio which is the ratio of the number of fibers oriented in the MD to the number of fibers oriented in the CD, where the fibers are associated with the felt side of the web, and determining the wire to felt ratio which is a measure of the tendency of the web to curl.

5 Claims, 5 Drawing Sheets

MEASUREMENT OF PAPER CURL TENDENCY USING SPECULAR AND DIFFUSE LIGHT REFLECTION

BACKGROUND OF THE INVENTION

The present invention relates to methods for the measurement of the tendency of a nonwoven web to curl.

Curl is an important mechanical property of nonwoven webs, such as paper. It is especially important to papers which are used in automated sheet-fed printing operations such as xerography. Excessive curl can cause the paper transport mechanism to jam, thereby creating a great deal of operator frustration, lost time, and service expense. Therefore, there is a need for a measuring device to predict the curl performance of webs which will be used in sheet-fed printing machines.

Existing curl-measuring instrumentation tends to be slow and cumbersome to use. Usually the web is put in an environment which is designed to produce curl, and then the resulting degree of curl is measured.

In one common test, hot-strip-curl (HSC), the curling environment is represented by a curved heated block against which the operator presses four strips of paper to be tested. Upon removal, the arc acquired by a paper strip is compared to a series of arcs marked on a template. The inverse of the radius of curvature of the closest matching arc is noted as the curl value. The values for four strips are combined to produce a differential curl number. Two of the four strips are cut parallel to the machine direction (MD) and two of the strips are cut parallel to the cross-machine direction (CD). For each direction, one strip is held felt side toward the heated block and the other is held wire side to the heated block.

Another common test, split-sheet contraction (SSC) ratio, uses one MD and one CD strip which are each split, using tape, into felt and wire side sections. Following removal of the tape, the resulting four strips are conditioned in a high humidity environment and the length is measured. The humidity is then reduced and the decrease in length is measured. The four length shrinkages are combined into a ratio indicative of curl called the split-sheet contraction ratio.

Operator's skill is required to prepare the sample, verify the suitability of the curling environment, and read the curl value. The reproducibility of the measurement is extremely low, since errors can be introduced at each stage.

SUMMARY OF THE INVENTION

Therefore, it is an object of the present invention to provide a measure of a web's propensity to curl, so that it is no longer necessary to actually put curl into the sheet or to change the dimensions of the sheet by exposing it to a humidity change.

It is another object of the invention to automate the measurement process so that it does not depend subjectively on the person doing the measuring.

It is another object of the invention to facilitate sample preparation and handling, so that the instrument will be more frequently used by papermill personnel, with more accurate and reproducible results.

The present invention relies on the fact that curl depends, in part, on differences of fiber orientation between the two surfaces of a web. It further relies on the fact that fiber orientation can be measured optically using a geometry that combine elements of paper gloss and brightness measurements.

TAPPI specification T480om-85 for the measurement of gloss recognizes that the gloss values are different when read in the machine direction (MD) and in the cross-machine direction (CD) of a sheet. It calls for the reporting of readings made in both directions which are averaged to give a gloss value.

The present invention recognizes that MD and CD differences in gloss readings are, in large measure, indicative of the relative MD and CD fiber populations, which in turn are related to the tendency of the sheet to curl. The present invention further recognizes that brightness values measured using diffuse reflection will be similarly affected by fiber orientation.

Although either specular or diffuse reflection alone could be used as the basis for a fiber orientation measurement predictive of paper curl, experience indicates that a combination of both measurements is preferable. One possible explanation for this is that certain sheet properties which effect gloss and brightness (but are not related to fiber orientation) produce errors which cancel. Measurements based on the method and using the apparatus of the present invention correlate well with standard curl measurements using the "Split-Sheet Contraction" (SSC) test and the "Hot Strip Curl" (HSC) test.

According to the present invention, a collimated beam of light illuminates a sample web. The chosen angle of illumination is about 75° from vertical. A portion of the incident light is reflected specularly and another portion of the light is reflected diffusely in the vertical direction, 0°. A light detector called the specular detector is oriented at the specular angle and measures the light reflected at the specular angle. A similar light detector called the diffuse detector is oriented directly over the sample web and measures the diffuse light reflected from the web.

In the initial position of the sample web, the MD of the web is parallel to the projection of the light beam on the plane of the web. For this orientation, the light received at the specular detector is proportional to the number of MD-oriented fibers illuminated. The light received at the diffuse detector is proportional to the number of CD-oriented fibers illuminated. The ratio of the specular signal (S) to the diffuse signal (D) is a measurement of the number of fibers oriented along the MD (M) divided by the number of fibers oriented along the CD (C). Therefore:

$$M/C = S/D \quad (1)$$

M/C is measured for both the felt side (F) and wire side (W) of the web.

$$F = M/C \text{ (felt side)} \quad (2)$$

$$W = M/C \text{ (wire side)} \quad (3)$$

$$W/F = M/C \text{ (wire side)} / M/C \text{ (felt side)} \quad (4)$$

The value for W/F is predictive of the tendency of the web to curl and the value correlates well with SSC and HSC standard tests.

In order to obtain information from the whole sheet, multiple measurements are made. The sheet is rotated and a series of measurements (typically made every 5° for a total of 72 measurements) of S and D are obtained. The relationship represented in Equation (1) holds true only at 0° and 180° with respect to the MD. At 90° and 270° the following relationship applies:

$$M/C = D/S \tag{5}$$

In general, at any angle, $\alpha$, of the projection of the collimated beam of light on the web with respect to MD, the value of M/C is given by the equation:

$$\frac{M}{C} = \left[ \frac{S^2\cos^2\alpha - D^2\sin^2\alpha}{D^2\cos^2\alpha - S^2\sin^2\alpha} \right]^{\frac{1}{2}} \tag{6}$$

At $\alpha = 0°$ and 180°, Equation (6) reduces to Equation (1) and, at $\alpha = 90°$ and 270°, Equation (6) reduces to Equation (5). The average of M/C, $<M/C>$, is found by multiplying the individual measurements of $(M/C)^2$ by a weighing factor, summing, and dividing by n, the number of measurements, and taking the square root:

$$<M/C> = \left[ \frac{\sum_\alpha \left[ \frac{S^2\cos^2\alpha - D^2\sin^2\alpha}{D^2\cos^2\alpha - S^2\sin^2\alpha} \right] 2\cos^2 2\alpha}{n} \right]^{\frac{1}{2}} \tag{7}$$

Measurements of S and D are made of the wire side of the web (giving $S_w$ and $D_w$ values) and of the felt side of the web (giving $S_f$ and $D_f$).

The weighing factor $2\cos^2 2\alpha$ accounts for the fact that no information about M/C is provided by a measurement of S/D at $\alpha = 45°$, 135°, 225° and 315° since Equation (6) gives $(M/C)^2 = 1.0$ at those angles, independent of the S/D values. At angles close to, but not equal to, odd multiples of 45°, $(M/C)^2$ may be calculated from Equation (6), but the result is noisier than for the values calculated at even multiples of 45°. This feature is also represented by the use of the weighing factor.

The amount of diffuse light received by the diffuse detector is generally much smaller than the amount of specular light received by the specular detector. Therefore the values of D and S must be scaled in order to get an accurate measurement of M/C. In the scaling process performed prior to the calculation of $<M/C>$, an average of all S values, $<S>$, and an average of all D values, $<D>$, are determined. Each individual D value is then multiplied by the ratio of $<S>$ to $<D>$, $<S>/<D>$. The new values of D then have the same average as the average of the S values.

An advantage of the present invention over prior practice is that it provides a measurement of fiber orientation, one of the fundamental sources of curl in paper. In contrast with prior practice, this advantage is obtained without actually having to put curl into the sheet. With existing curl-measuring instrumentation the paper is usually put in an environment designed to produce curl and then the resulting degree of curl is measured. The observed curl could result from fiber orientation or from some other source of two-sidedness in the sheet. Since the degree to which fiber orientation contributes to curl is not known, it is difficult to use the results of existing curl tests to control the paper machine. The present invention can be combined with existing curl tests to determine whether fiber orientation or some other source of two sidedness is operative, thus facilitating paper-machine control.

Present curl-measuring techniques often require visual readings from a scale or dial. Also operator's skill is required to prepare the sample, verify the suitability of the curling environment, and read the curl value. The reproducibility of the measurement is extremely low, since errors can be introduced at each stage of the measurement. The present invention automates the measuring process so that it does not depend subjectively on the person doing the measuring. Further, the present invention facilitates the sample preparation and handling so that curl measurements will be made more frequently by papermill personnel with more accurate and reproducible results.

BRIEF DESCRIPTION OF THE DRAWINGS

The present invention may be better understood by reference to the following detailed description of an exemplary embodiment when considered in conjunction with the drawings in which.

DESCRIPTION OF THE PREFERRED EMBODIMENT

Figure 1:
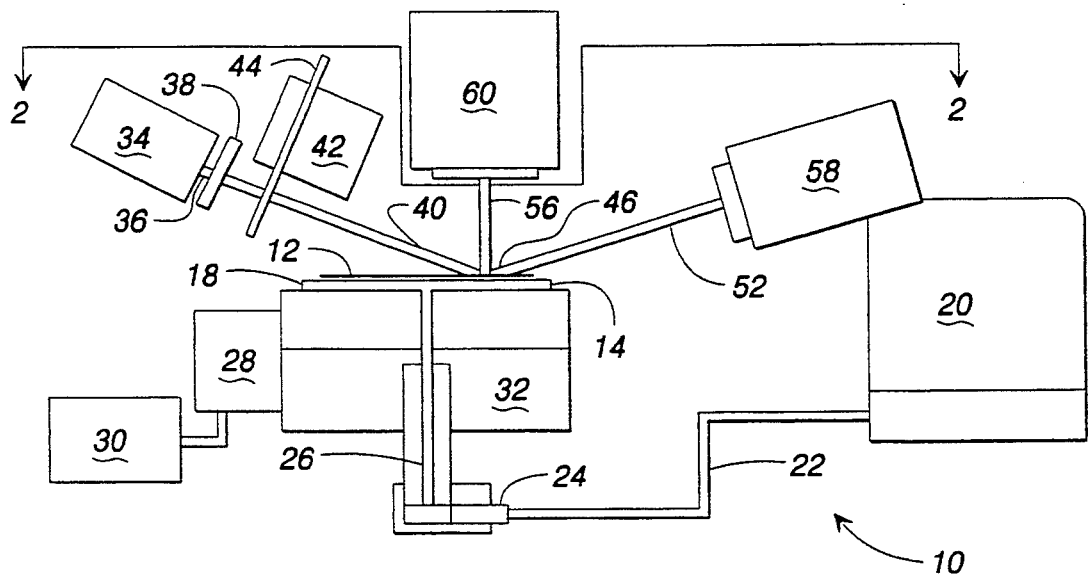
FIG. 1 is a side view of an embodiment of the present invention for predicting the tendency of paper to curl using specular light reflection.
Figure 2:
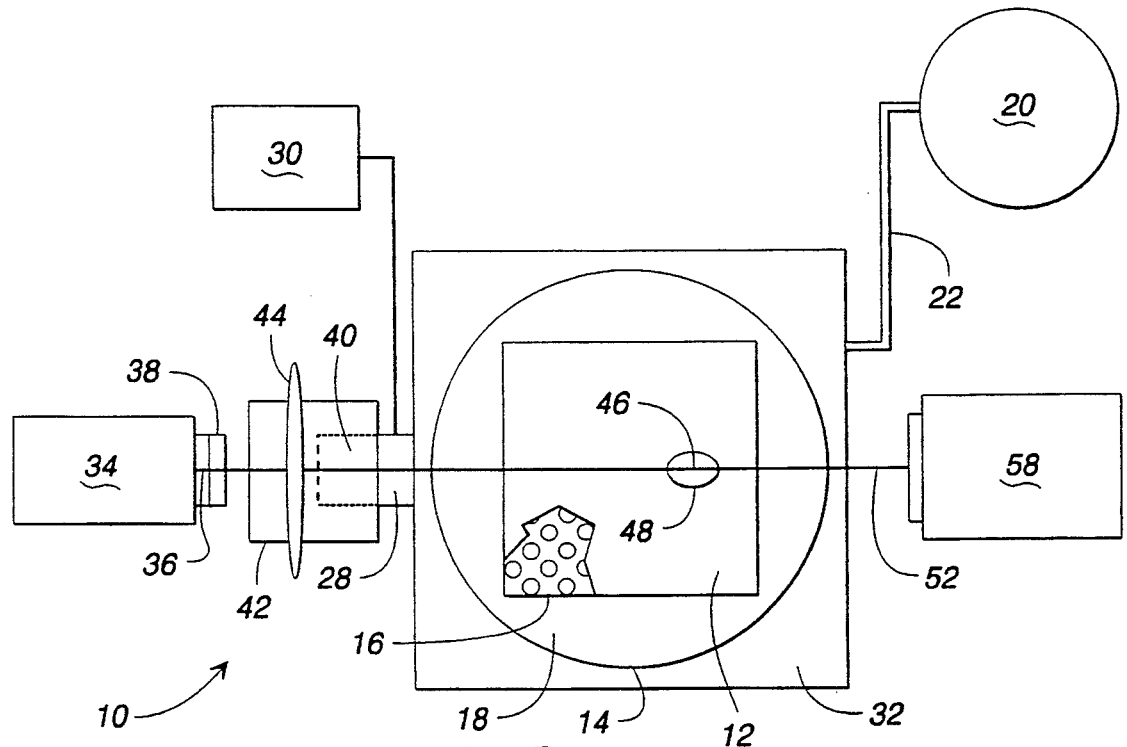
FIG. 2 is a view of FIG. 1 taken along the cross-section 2—2.

Referring now to the drawings in which like reference characters designate like or corresponding parts throughout the several views, there is shown in FIGS. 1 and 2 an apparatus 10 which is an embodiment of the present invention. The depicted apparatus 10 includes a sheet of paper 12 for which the tendency to curl is to be predicted. The sheet 12 is secured to a vacuum table 14 by suction. Vacuum table 14 has holes 16 in its top surface 18. Air is drawn into the holes 16 by a vacuum pump 20 which is connected to the vacuum table 14 by a vacuum hose 22, a vacuum coupling 24, and a connecting spindle 26. The vacuum pump 20 draws air through the holes 16 and thereby releasably secures the sheet 12 to the top surface 18 of the vacuum table 14.

A stepper motor 28 is controlled by a stepper motor driver 30. The stepper motor 28 positions the vacuum table 14 to any one of seventy-two positions at 5° intervals. The vacuum table 14, connecting spindle 26, and stepper motor 28 are mounted in a rotary table 32 in order to insure that the vacuum table 14 rotates in a constant plane and with a minimum of vibration.

A laser 34 directs a laser beam 36 through a cylinder lens 38 producing an incident beam of light 40. A chopper 42 is placed in the line of the incident beam 40 with a chopper wheel 44 alternately blocking and then passing the incident beam 40. The incident beam 40 strikes the paper at a position 46, not coincident with the axis of the connecting spindle 26, and produces an elliptical pattern 48 on the sheet 12. The incident beam 40 strikes the sheet 12 at the incident angle of about 75° from the normal to the sheet 12.

Figure 3:
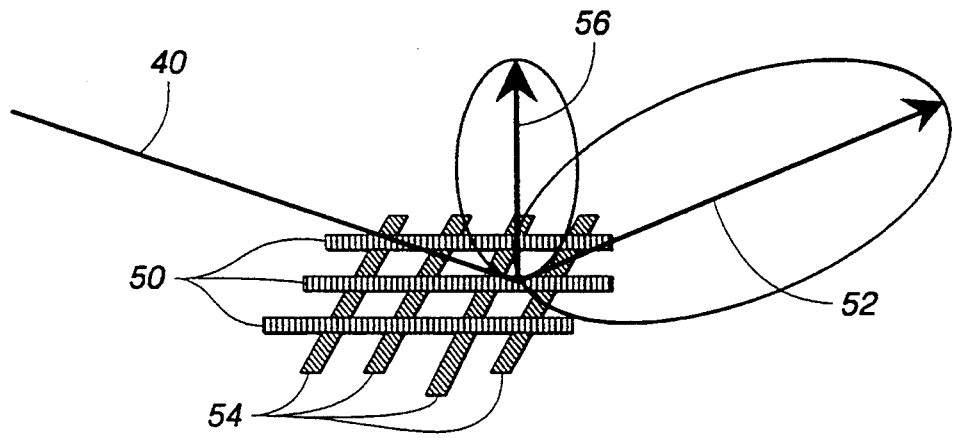
FIG. 3 is a schematic drawing showing the locus of light reflected from fibers parallel to and orthogonal to the projection of an incident beam of light.

FIG. 3 shows a schematic of the tendency of light reflected from fibers parallel to and orthogonal to an incident beam of light 40. Those fibers 50 of the sheet, which are oriented parallel to the projection of the incident beam 40, tend to reflect the light at the specular angle producing a specular beam 52 of light. Those fibers 54, which are orthogonal to the incident beam 40 and the parallel fibers 50, tend to reflect the light at an angle perpendicular to the sheet 12 producing a diffuse beam of light 56.

Therefore, if the sheet 12 is oriented so that the parallel beam 40 is parallel to the machine direction, MD, then the MD fibers produce a specular beam of light 52 and the CD fibers produce a diffuse beam of light 56. If the sheet 12 is oriented so that the parallel beam 40 is parallel to the cross machine direction (CD), then the CD fibers would produce the specular beam 52 and the MD fibers would produce the diffuse beam 56.

Figure 4:
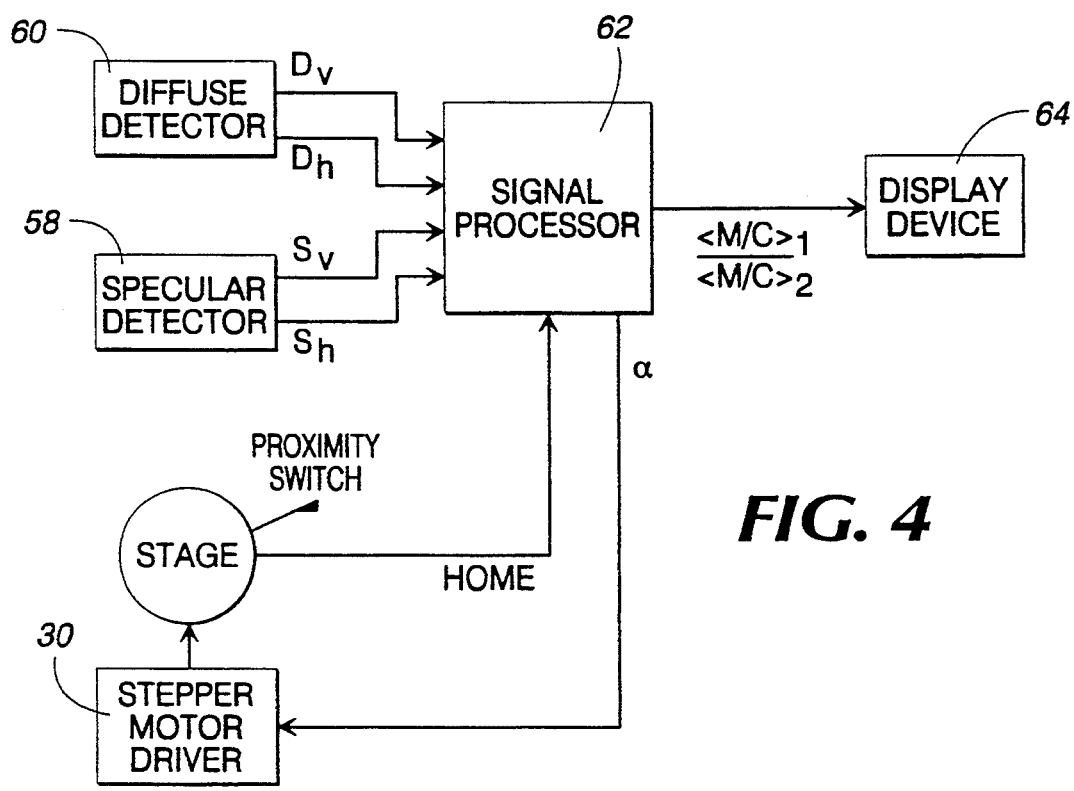
FIG. 4 is a block diagram of the signal processing used in an embodiment of the present invention to predict the tendency of a nonwoven web sheet to curl.

Referring again to FIGS. 1 and 2, the specular beam 52 is reflected from the sheet 12 and into a specular detector 58. The diffuse beam 56 is reflected from the sheet 12 and into the diffuse detector 60. As is shown in FIG. 4, the outputs of the diffuse detector 60 and the specular detector 58 are routed to a signal processor 62. The signals from the diffuse detector 60 are the values $D_H$ and $D_V$ and the signals from the specular detector 58 are the value $S_H$ and $S_V$. The angular position, $\alpha$, of the sheet 12 is sent from the signal processor 62 to the stepper motor driver 30.

The subscripts H and V indicate signals generated by horizontal (H) and vertical (V) polarized light in the reflected beams, where the incident beam polarization is horizontal. The signal processor uses these polarization components to calculate the S and D signals used in the determination of M/C.

Figure 5:
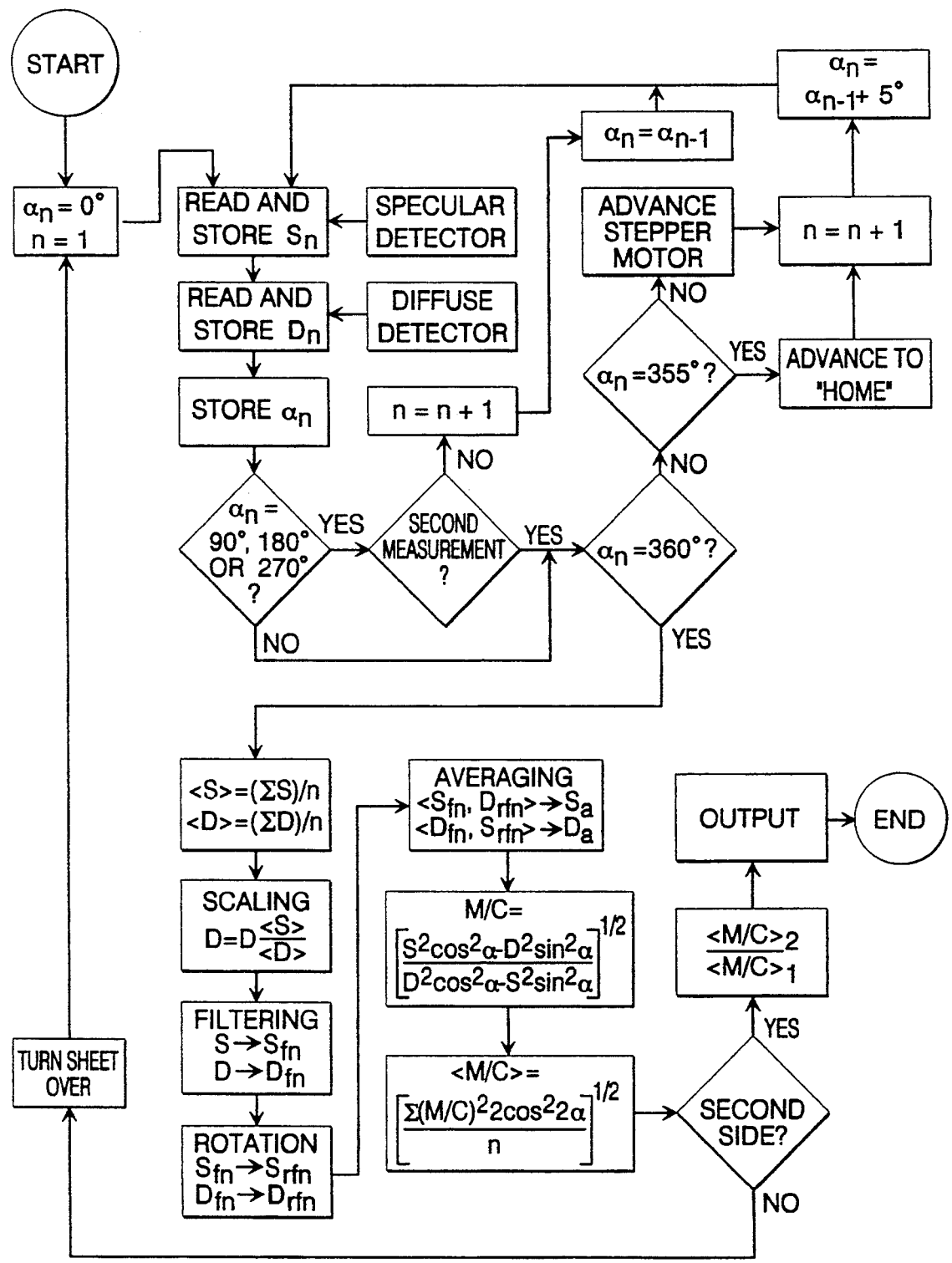
FIG. 5 is a flow diagram of the computation of the tendency of a nonwoven web sheet to curl.

FIG. 5 shows a flow chart of how the S and D signals are processed by the signal processor 62. Upon start-up of the program, the values of $\alpha$ and an indexing integer, n, are initialized. The value of S at the angle $\alpha$ is determined by the signal processor 62 from the values $S_H$ and $S_V$ read from the specular detector 58 and stored for later use. Similarly, the values of D at $\alpha$ is determined and stored. At $\alpha$ values of 90°, 180° and 270°, two measurements of $S_n$ and $D_n$ are read and stored. The first of the two measurements is associated with the largest angle in the quadrant just completed. The second of the two measurement is associated with the smallest angle in the quadrant just begun. This allows us to parcel the data into independent arrays that represent each of four quadrants, with the angle ranging from 0 to 90 degrees (inclusive) within each quadrant. This is a convenient way to handle the data, but not the only way. For simplicity, we will describe the angle arrays in terms of a single index n such that angles range from 0 to 360 degrees.

When the reading and storing of S and D values is completed at any angle, the value of $\alpha$ is then incremented. If $\alpha$ does not yet equal 360°, then the stepper motor driver 30 is triggered to rotate the vacuum table 14 one step (approximately 5°). If $\alpha=355°$, the stepper motor driver is triggered to rotate the vacuum table 14 to the "home" position as indicted by a proximity switch. The indexing integer is updated and S and D are determined and stored again. When $\alpha=360°$, the signal processor 60 computes the average values of S and D to obtain $<S>$ and $<D>$. The value of D is normalized by multiplying D by $<S>/<D>$.

Figure 6:
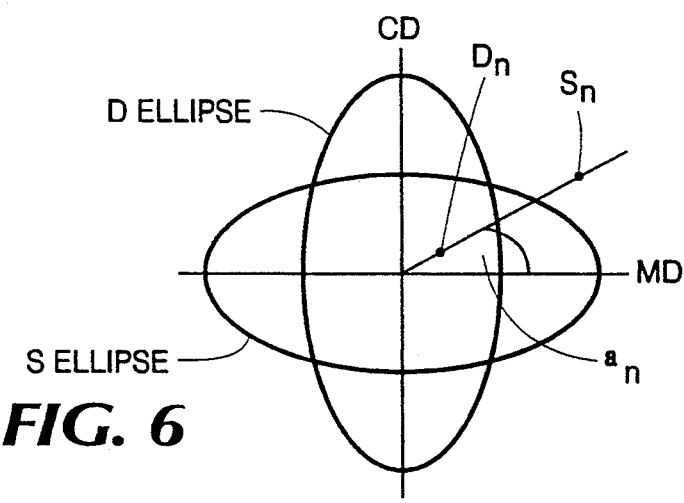
FIG. 6 is a schematic drawing of the elliptical patterns associated with the specular and diffuse light detectors as the sheet is rotated through 360°.

At this point, $S(\alpha)$ and $D(\alpha)$ are each arrays in signal processing memory which, when plotted, are approximately elliptical in shape and rotated by about 90° with respect to each other. Individual elements of the arrays are generally positioned on one side or the other of best fitting ellipses as determined from the arrays by the signal processor. With reference to FIG. 6, an angle, $\alpha_n$, has measurements, $D_n$, less than the value associated with the best fitting ellipse for array D. In contrast, $S_n$ is greater than the best fitting ellipse for array S.

This situation could arise from a glossy spot of the sheet at the point of the nth measurement. Alternatively, there could be an excess of MD or CD fiber orientation at that location relative to the average for the sample as a whole. In either case, the following approach is used to filter the data to improve the measurement: the average percent deviation of each datum from the corresponding best fitting curve is determined; each point is then moved toward the best fitting curve by an amount equal to that average deviation times a weighing factor.

For example, let $\%D_n$ be the percent deviation of the point $D_n$ below the theoretical D curve, and let $\%S_n$ be the percent deviation of the point $S_n$ above the theoretical S curve. The average percent deviation, $\%A$, is calculated as:

$$\% A = \frac{\% S_n + \% D_n}{2} \qquad (8)$$

The weighing factor, $W_n$, is:

$$W_n = \left| \frac{\text{minimum of } (|\% S_n|, |\% D_n|)}{\% A} \right| \qquad (9)$$

Therefore, the weighing factor is 0 if either point $D_n$ or $S_n$ is on the appropriate theoretical curve, and it is 1 if $\%D_n = \%S_n$. The weighting factor is also taken to be 0 if both $D_n$ and $S_n$ are of the same side of their respective theoretical curves. The reason is that phenomena such as gloss or fiber orientation variation do not tend to lead to deviations on the same side of the theoretical curves.

The filtering process produces new array elements $D_{fn}(\alpha)$ and $S_{fn}(\alpha)$:

$$D_{fn} = D_n[1 + W_n \% D_n / 100\%] \qquad (10)$$

$$S_{fn} = S_n[1 - W_n \% S_n / 100\%] \qquad (11)$$

The $D_{fn}(\alpha)$ array is then rotated 90° so that it is brought into alignment with the $S_{fn}(\alpha)$ array. That is, the best fitting ellipses from each array have parallel major and minor axes. The rotated array, $D_{rf}(\alpha)$, is given by:

$$D_{rf}(\alpha)=D_f(\alpha-90°) \quad (12)$$

The average array, $S_a(\alpha)$, is:

$$S_a(\alpha) = \frac{S_f(\alpha) + D_{rf}(\alpha)}{2} \quad (13)$$

In the same way, the $S_f(\alpha)$ array is rotated by 90° to form the rotated array, $S_{rf}(\alpha)$:

$$S_{rf}(\alpha)=S_{fn}(\alpha+90°) \quad (14)$$

The average, $D_a(\alpha)$, between the $S_{rf}(\alpha)$ array and the $D_{fn}(\alpha)$ array is:

$$D_a(\alpha) = \frac{D_f(\alpha) + S_{rf}(\alpha)}{2} \quad (15)$$

The $S_a(\alpha)$ and $D_a(\alpha)$ arrays are identical except for a 90° rotation of one with respect to the other. Equation (6) is then applied to calculate the M/C array, where $S_a(\alpha)$ and $D_a(\alpha)$ are substituted for S and D respectively.

The average of M/C is computed from Eq. (7) to obtain <M/C> which is then stored for further use. Once the felt side of sheet 12 has been measured, the wire side is measured to obtain a wire value of <M/C>. The ratio of the wire <M/C> to the felt <M/C> is computed which gives the tendency of the sheet 12 to curl. As is shown in FIG. 4, the ratio is sent to a display device 64, such as a printer or video display terminal for use by an operator.

Figure 7:
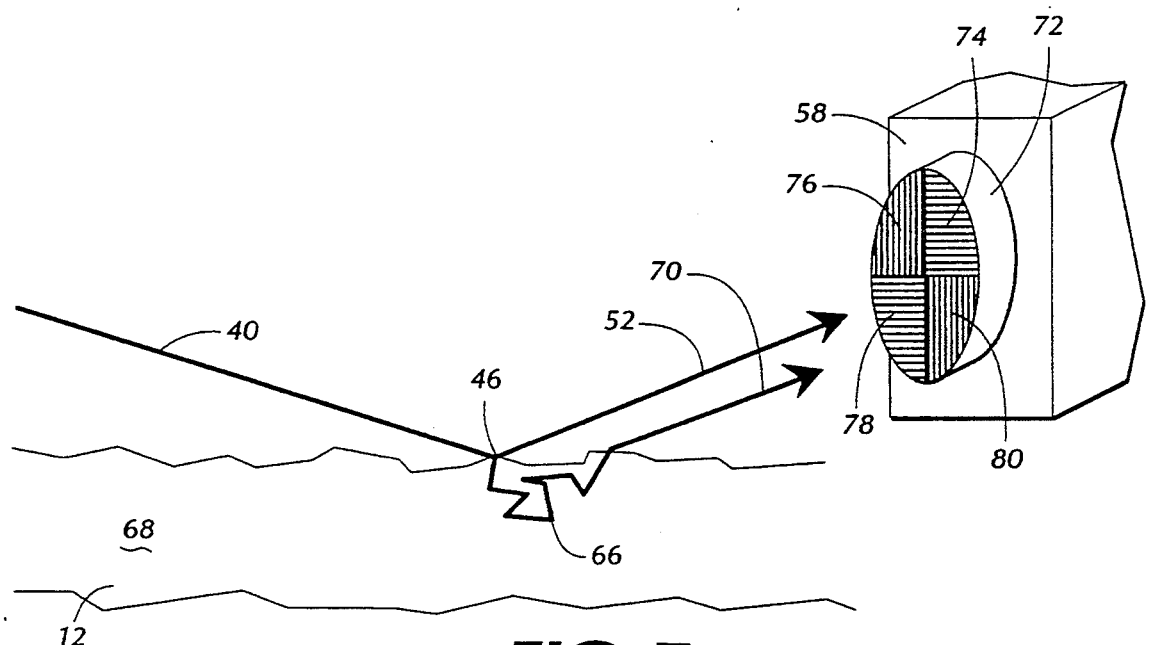
FIG. 7 is a schematic drawing of specularly reflected light from the surface and forward-scattered light from the volume of a nonwoven web sheet.

In order for the apparatus 10 to work at high levels of accuracy, it is necessary to compensate for light that back-scatters in the sheet 12. This is illustrated in FIG. 7 which is a schematic drawing of specularly reflected and back-scattered light from a sheet 12. The incident beam of light 40, which is horizontally polarized, strikes the sheet 12 at position 46. A portion of the parallel beam 40 is reflected as the specular beam 52, still horizontally polarized, but a portion of the light 66 passes into the interior 68 of the sheet 12 where it is scattered by the fibers in the sheet 12. Some of the light 66 escapes from the sheet 12 as an unpolarized beam of light 70. The specular detector 58 receives light from both the specular beam 52 and the unpolarized beam 70. The specular detector 58 comprises a set 72 of four photodiode detectors with oriented polarizers 74–80. Two of the polarizers 74, 78 are oriented to admit only horizontally polarized light while the other two polarizers 76, 80 are oriented to admit only vertically polarized light. Since the unpolarized beam has an equal amount of horizontally and vertically polarized photons, subtracting the vertically polarized signal from the horizontally polarized signal gives the signal attributable solely to the specular beam 52.

Figure 8:
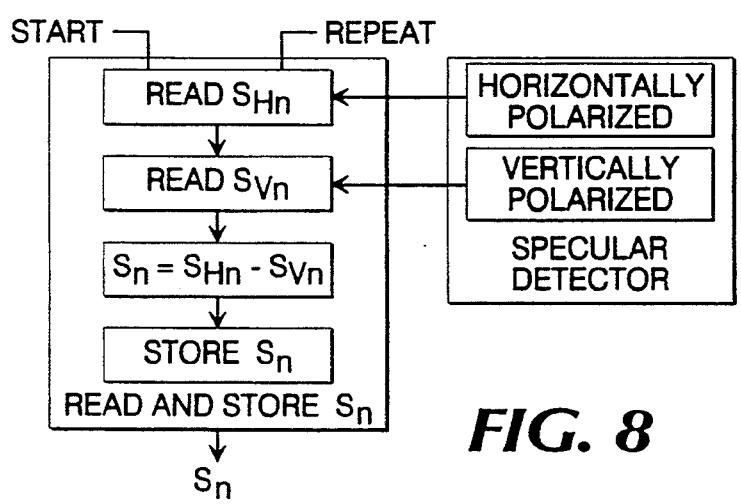
FIG. 8 is a flow diagram of the computation of the value of specularly reflected light from the surface of a nonwoven web sheet.

The flow chart of FIG. 8 shows the computation that occurs in the signal processor 62 to compensate for the presence of the unpolarized beam 70 at the specular detector 58. The signal, $S_{Hn}$, from the horizontally polarized detectors and the signal, $S_{vn}$, from the vertically polarized detectors of the set of four photodiode detectors 72 are read by the signal processor 62 in the read and store $S_n$ block. The vertical signal is subtracted from the horizontal signal to give the value of the specular beam 52:

$$S_n=S_{Hn}-S_{Vn} \quad (16)$$

The value of the spectral beam 52 is then used as was described previously.

Figure 9:
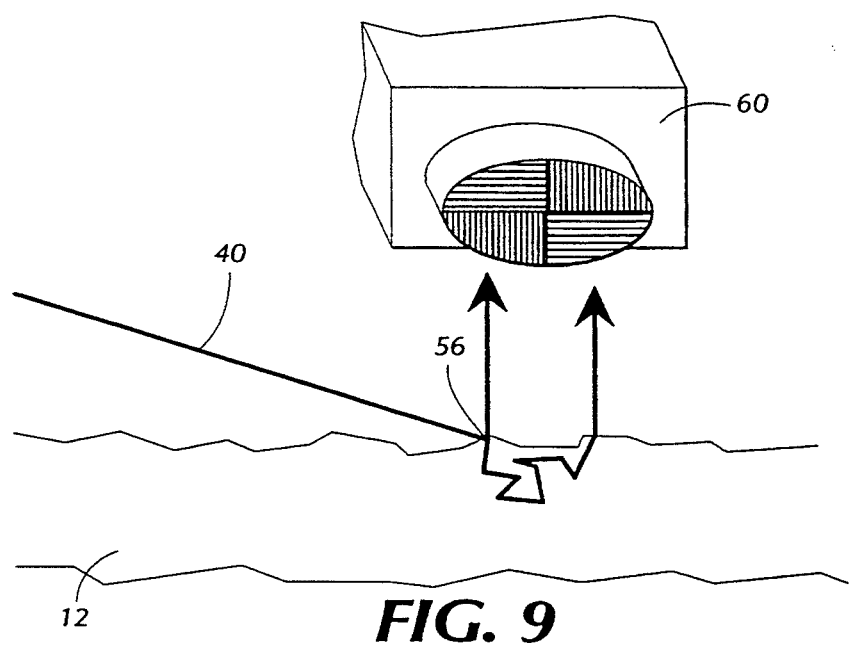
FIG. 9 is a schematic drawing of diffusely reflected light from the surface and upwardly back-scattered light from the volume of a nonwoven web sheet.

In the same way, FIG. 9 shows schematically how diffusely reflected light from the sample 12 is collected by two horizontal and two vertical detectors that, in total, comprise the diffuse detector 60. The vertical signal is again subtracted from the horizontal signal to give the value, $D_n$, of the diffuse beam 56:

$$D_n=D_{Hn}-D_{Vn} \quad (17)$$

In order to provide a more complete understanding of the present invention, the following examples are given primarily for the purposes of illustrating certain more specific details thereof.

EXAMPLE I

Split-Sheet Contraction (SSC) Test

Tape was applied to both sides of a thin strip of paper to be tested. The paper strip was delaminated when the two strips of tape were pulled apart. Roughly one-half of the paper strip remains with each tape strip. The tape was dissolved by toluene and the resulting paper strips were suspended under very mild tension in a variable humidity chamber. The tendency of the strips to expand or contract under varying conditions was measured. By measuring felt-side and wire-side strips cut in both the machine direction (MD) and cross-machine direction (CD), the tendency of the sheet to curl was measured as a ratio. The results for various types of papers are given in Table I. Each value represents a value that is an average from five sheets.

EXAMPLE II

Curl Prediction According to Present Invention

A four-inch by four inch sheet of paper was oriented in the MD in an apparatus as shown in FIGS. 1 and 2. The M/C values were determined at 5° increments around the circumference of a 1.5 inch diameter circle on the felt-side of the sheet. The values of M/C were averaged. The sheet was turned over and the wire-side M/C values were determined. A wire-to-felt M/C ratio was determined. The results for various papers are given in Table I. Each value represents a value that is an average from five sheets.

TABLE I

| Sample | SSC[a] | W/F[b] |
|--------|--------|--------|
| A | 0.817 | 0.955 |
| B | 0.814 | 0.950 |
| C | 0.949 | 1.021 |
| D | 1.030 | 1.056 |
| E | 1.133 | 1.123 |
| F | 1.255 | 1.075 |

Figure 10:
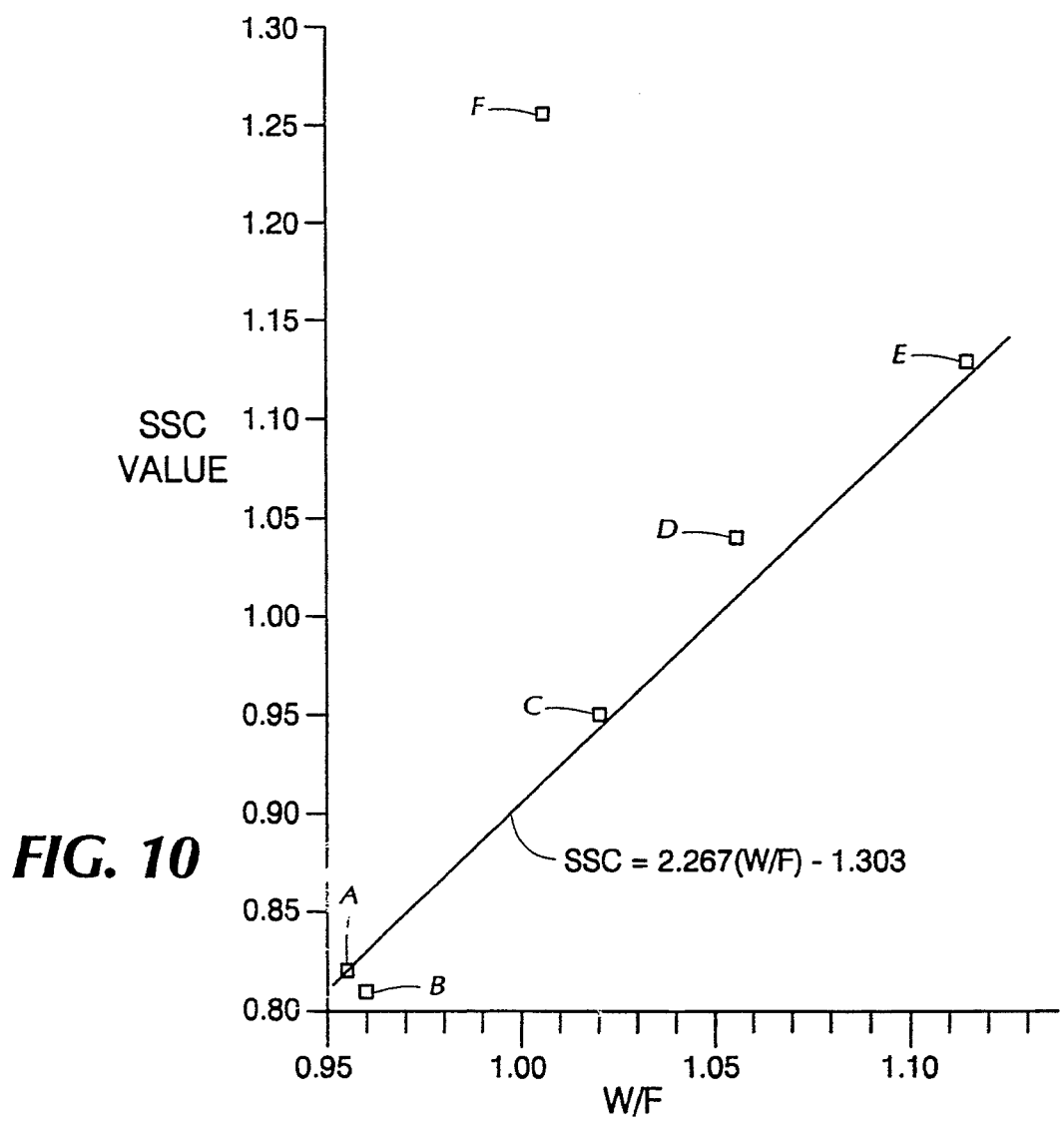
FIG. 10 is a graph showing the correlation of the method of the present invention (W/F) with the split-sheet contraction (SSC) test of the prior art.

[a]Split-Sheet Contraction
[b]Wire-side to Felt-side ratio of <M/C>, the method of the present invention FIG. 10 shows the correlation of the method of this invention compared to the standard SSC method. With the exception of outlier, sample F, the correlation is excellent between the two methods of measurement. Excluding Sample F, the relationship between the measurement of curl by SSC and the measurement of the tendency to curl by W/F is defined by a line with the equation $$SSC = 2.267 (W/F) - 1.383$$

with a standard error of estimate of 0.039. This shows a consistent relationship between SSC and the method of the present invention. Thus, the present invention provides an accurate, automatic and efficient means of determining the tendency of a paper sheet to curl. Outlying points like sample F are interpreted as showing the influence of sources of sheet two-sidedness other than fiber orientation. Presumably, the influence of these sources is constant in samples A through E, resulting in the observed good correlation. Thus, the present invention provides an accurate, automatic, and efficient means of determining changes in paper curl associated with changes in fiber orientation, when other sources of two-sidedness are held constant.

Although a particular embodiment of the invention has been discussed, it will be understood that this is an example that was described for the purposes of illustration and that the invention is capable of numerous rearrangements, modifications and substitutions of part without departing from the spirit of the invention. In particular, it is noted that the sheet of paper may be maintained in a constant position while the light source and photodetector may be rotated around a spot of light. Optionally, both the first surface and the second surface may be measured at the same time. In yet another embodiment a series of light photodetectors may be arranged to detect a plurality of beams of light projected on one or both surfaces of a sample. The present invention need not be restricted to laboratory use but may be adapted for on-line use with a papermaking machine.

Alternative approaches to the signal processing of the elliptical $S(\alpha)$ and $D(\alpha)$ arrays described above are possible. For example, one can compute the wire-to-felt ratio for individual array elements, then average the ratios to produce a composite average for the sheet.

Other algorithms than those embodied in Equations (1)–(7) are possible for reducing data that generally follows the shape of an ellipse, including algorithms for calculating the tilt of the ellipse relative to the geometric machine direction. The tilt angle, called the fiber orientation angle, is also useful for the prediction of web performance. The present invention provides the opportunity for calculating the tilt angle on the wire and felt sides of the web independently. In addition, the wire and felt differences of the specular and diffuse signals themselves may also be of interest for predicting curl and other hygroexpansive properties of the web. The differences are also measurable according to the present invention.

Various of the features of the invention which are believed to be new are set forth in the appended claims.

What is claimed is:

1. A method for determining the tendency of a non-woven web to curl, wherein said web has a machine direction, MD, a cross-machine direction, CD, and said web includes a wire side and a felt side, said method comprising:
   determining a wire ratio, $(M/C)_w$, which is the ratio of the number of fibers oriented in the MD to the number of fibers oriented in the CD, wherein said fibers are associated with the wire side of said web;
   determining a felt ratio, $(M/C)_f$, which is the ratio of the number of fibers oriented in the MD to the number of fibers oriented in the CD, wherein said fibers are associated with the felt side of said web; and
   determining a wire to felt ratio, $(M/C)_w/(M/C)_f$, which is the ratio of the wire ratio to the felt ratio, whereby the wire to felt ratio is a measure of the tendency of said web to curl.

2. The method of claim 1 wherein the steps of determining the wire ratio and determining the felt ratio further comprise:
   projecting a beam of light onto the wire side of said web at an incident angle;
   measuring the amount of light, $S_w$, reflected from the surface of said web at the specular angle;
   measuring the amount of light, $D_w$, reflected from the surface of said web normal to the wire side of said web;
   determining the wire ratio according to the equation:

$$(M/C)_w = \left[ \frac{S_w^2 \cos^2\alpha - D_w^2 \sin^2\alpha}{D_w^2 \cos^2\alpha - S_w^2 \sin^2\alpha} \right]^{\frac{1}{2}},$$

wherein $\alpha$ is the angle of the projection of the beam of light on said web with respect to the MD of said web;
   projecting a beam of light onto the felt side of said web at the incident angle;
   measuring the amount of light, $S_f$, reflected from the surface of said web at the specular angle;
   measuring the amount of light, $D_f$, reflected from the surface of said web normal to the felt side of said web; and
   determining the felt ratio according to the equation:

$$(M/C)_f = \left[ \frac{S_f^2 \cos^2\alpha - D_f^2 \sin^2\alpha}{D_f^2 \cos^2\alpha - S_f^2 \sin^2\alpha} \right]^{\frac{1}{2}}.$$

3. The method of claim 2 wherein the amount of light, S, and the amount of light, D, are measured at a plurality of angles, $\alpha$, wherein $\alpha$ is the angle of the beam of light with respect to the MD of said web, the wire ratio is determined by the equation:

$$(M/C)_w = \left[ \frac{\sum_\alpha \left[ \frac{S_w^2 \cos^2\alpha - D_w^2 \sin^2\alpha}{D_w^2 \cos^2\alpha - S_w^2 \sin^2\alpha} \right] 2\cos^2 2\alpha}{n} \right]^{\frac{1}{2}},$$

wherein n is the number of angles at which S and D are measured, and the felt ratio is determined by the equation:

$$(M/C)_f = \left[ \frac{\sum_\alpha \left[ \frac{S_f^2 \cos^2\alpha - D_f^2 \sin^2\alpha}{D_f^2 \cos^2\alpha - S_f^2 \sin^2\alpha} \right] 2\cos^2 2\alpha}{n} \right]^{\frac{1}{2}},$$

and wherein the value of D is normalized to the value of the ratio of the average of S to the average of D.

4. An apparatus for determining the tendency of a non-woven web to curl, wherein said web has a machine direction, MD, a cross-machine direction, CD, and said web includes a wire side and a felt side, said apparatus comprising:

means for mounting said web in a plane;

a source of light, wherein said light is collimated into a beam of light angled to project onto the plane of said web at an incident angle;

a specular detector for detecting the amount of light, S, reflected from the surface of said web at the specular angle from the plane of said web;

a diffuse detector for detecting the amount of light, D, reflected from the surface of said web normal to the plane of said web; and a signal processor for processing S and D and thereby determine the tendency of said nonwoven web to curl, whereby said signal processor determines a wire ratio, $(M/C)_w$, which is a measure of the ratio of the number of fibers associated with the wire side of said web oriented in the MD to the number of fibers associated with the wire side of said web oriented in the CD, according to the equation:

$$(M/C)_w = \left[ \frac{S_w^2\cos^2\alpha - D_w^2\sin^2\alpha}{D_w^2\cos^2\alpha - S_w^2\sin^2\alpha} \right]^{\frac{1}{2}},$$

wherein $\alpha$ is the angle of the beam of light with respect to the MD of said web, said signal processor determines a felt ratio, $(M/C)_f$, which is a measure of the ratio of the number of fibers associated with the felt side of said web oriented in the MD to the number of fibers associated with the felt side of said web oriented in the CD, according to the equation:

$$(M/C)_f = \left[ \frac{S_f^2\cos^2\alpha - D_f^2\sin^2\alpha}{D_f^2\cos^2\alpha - S_f^2\sin^2\alpha} \right]^{\frac{1}{2}},$$

and said signal processor determines a wire to felt ratio, $(M/C)_w/(M/C)_f$, which is the ratio of the wire ratio to the felt ratio, wherein the wire to felt ratio is a measure of the tendency of said web to curl.

5. The apparatus of claim 4 wherein said means mounting said web further comprises:

a vacuum table for mounting said web in a plane and for rotating said web about an axis perpendicular to said plane;

a vacuum coupling for providing suction to said web to hold it in place; and a pedestal for mounting said vacuum table, whereby S and D are measured at a plurality of angles, $\alpha$, the wire ratio is determined according to the equation:

$$(M/C)_w = \left[ \frac{\sum_\alpha \left[ \frac{S_w^2\cos^2\alpha - D_w^2\sin^2\alpha}{D_w^2\cos^2\alpha - S_w^2\sin^2\alpha} \right] 2\cos^2 2\alpha}{n} \right]^{\frac{1}{2}},$$

wherein n is the number of angles at which S and D are measured, and the felt ratio is determined according to the equation:

$$(M/C)_f = \left[ \frac{\sum_\alpha \left[ \frac{S_f^2\cos^2\alpha - D_f^2\sin^2\alpha}{D_f^2\cos^2\alpha - S_f^2\sin^2\alpha} \right] 2\cos^2 2\alpha}{n} \right]^{\frac{1}{2}}.$$

* * * * *